(12) United States Patent
McLennan et al.

(10) Patent No.: US 10,034,975 B2
(45) Date of Patent: Jul. 31, 2018

(54) THERMAL MANAGEMENT SYSTEM AND METHOD FOR MEDICAL DEVICES

(71) Applicant: ICU Medical, Inc., San Clemente, CA (US)

(72) Inventors: Kevin P. McLennan, Chicago, IL (US); John C. Hoenninger, III, Deerfield, IL (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 15/592,059

(22) Filed: May 10, 2017

(65) Prior Publication Data

US 2017/0340809 A1 Nov. 30, 2017

Related U.S. Application Data

(63) Continuation of application No. 14/538,339, filed on Nov. 11, 2014.

(60) Provisional application No. 61/902,495, filed on Nov. 11, 2013.

(51) Int. Cl.
*A61M 5/14* (2006.01)
*A61M 5/142* (2006.01)
*H05K 7/20* (2006.01)
*G06F 1/20* (2006.01)

(52) U.S. Cl.
CPC ............ *A61M 5/1415* (2013.01); *A61M 5/14* (2013.01); *A61M 5/142* (2013.01); *G06F 1/20* (2013.01); *H05K 7/20* (2013.01); *H05K 7/20436* (2013.01); *A61M 2205/3372* (2013.01); *A61M 2209/082* (2013.01)

(58) Field of Classification Search
None
See application file for complete search history.

(56) References Cited

U.S. PATENT DOCUMENTS

| 3,901,231 | A |   | 8/1975 | Olson |
| 3,985,133 | A |   | 10/1976 | Jenkins et al. |
| 5,395,320 | A | * | 3/1995 | Padda ............... A61M 5/14228 128/DIG. 12 |
| 5,616,124 | A |   | 4/1997 | Hague et al. |

(Continued)

FOREIGN PATENT DOCUMENTS

WO    WO 99/010830    3/1999

*Primary Examiner* — Dimary Lopez Cruz
*Assistant Examiner* — Zhengfu Feng
(74) *Attorney, Agent, or Firm* — Knobbe, Martens, Olson & Bear, LLP

(57) ABSTRACT

A medical device includes a housing, a power supply, a thermally conductive mounting clamp, a heat shield, and at least one fastener. The housing includes a handle. The power supply is disposed within the housing. The thermally conductive mounting clamp is attached to an outer surface of the housing. The heat shield is disposed within the housing adjacent to the power supply. The heat shield is disposed against at least one interior surface of the handle. The at least one fastener passes through at least one opening in the housing and is in thermally conductive contact with the thermally conductive mounting clamp. Heat generated by the power supply is configured to dissipate from the power supply, through the heat shield, through the at least one fastener, and into the thermally conductive mounting clamp.

20 Claims, 6 Drawing Sheets

(56) References Cited

U.S. PATENT DOCUMENTS

| | | | |
|---|---|---|---|
| 5,782,805 | A | 7/1998 | Meinzer et al. |
| 7,061,766 | B2 | 6/2006 | Wainwright et al. |
| 7,975,491 | B2 | 7/2011 | Smission et al. |
| 8,052,644 | B2 | 11/2011 | Radgowski et al. |
| 8,286,977 | B2 | 10/2012 | Butler et al. |
| 2005/0168941 | A1 | 8/2005 | Sokol et al. |
| 2007/0233003 | A1* | 10/2007 | Radgowski ......... A61M 1/0058 604/151 |
| 2011/0213395 | A1 | 9/2011 | Corrington et al. |
| 2012/0035418 | A1 | 2/2012 | Talbert et al. |

\* cited by examiner

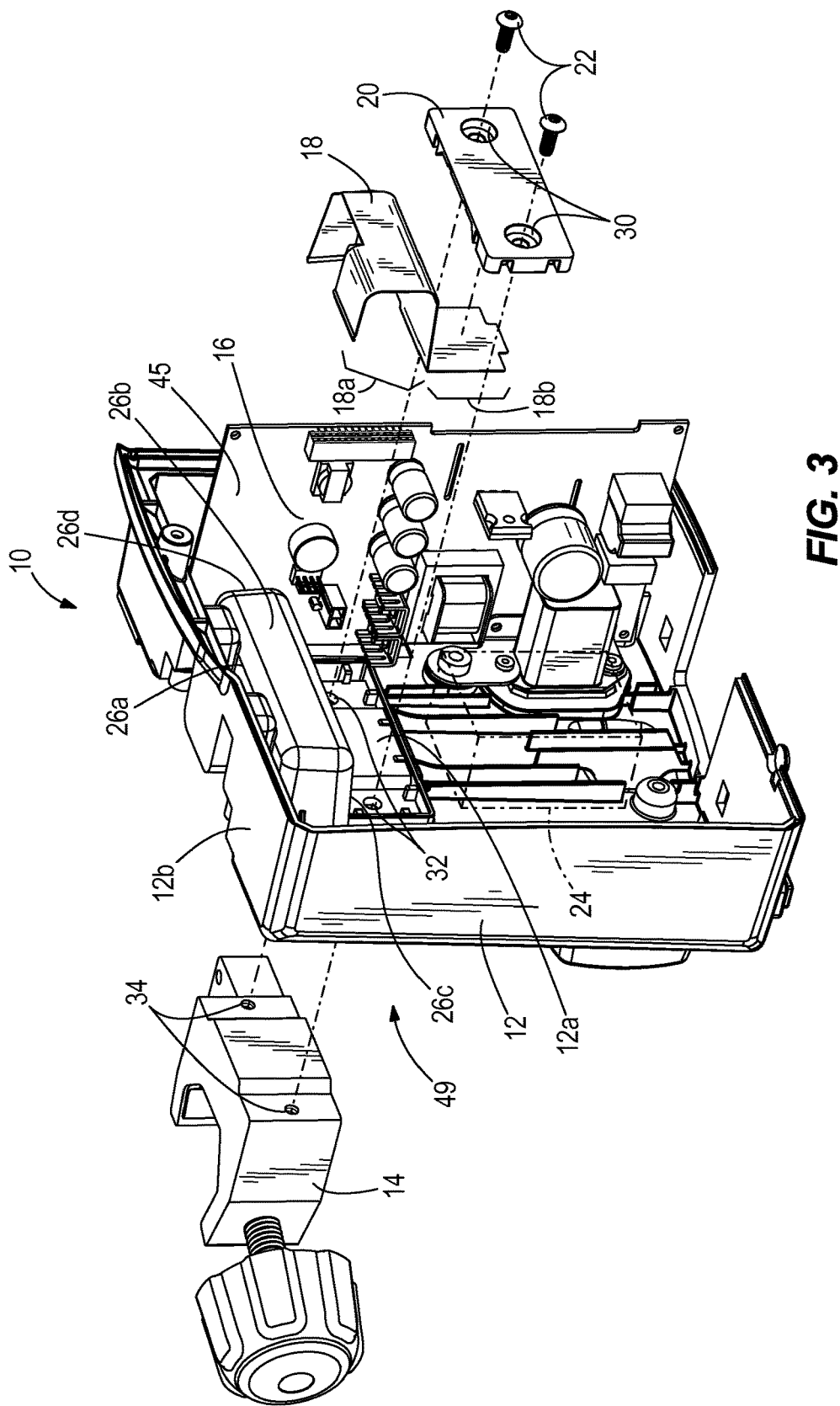

US 10,034,975 B2

THERMAL MANAGEMENT SYSTEM AND METHOD FOR MEDICAL DEVICES

FIELD OF THE DISCLOSURE

The disclosure relates to a system and method for providing thermal management in medical devices.

BACKGROUND OF THE DISCLOSURE

Medical devices, such as infusion pumps, typically generate substantial heat. Certain medical electrical equipment standards, such as IEC 60601-1 $3^{rd}$ Edition, require the temperature of external surfaces of the medical device to not exceed specified limits to prevent discomfort to the user. For example, IEC 60601-1 $3^{rd}$ Edition requires the temperature of touchable molded plastic surfaces of the medical device to be 60 degrees Celsius or below under certain ambient and use conditions. Some conventional approaches to meeting this requirement are to place a fan within the housing, or to place air vents in one or more outer walls of the housing to dissipate the heat generated by the infusion pump circuitry. However, a fan requires additional power and air vents may allow fluid to enter the housing.

A safe, efficient, and low cost system and method of dissipating heat in a medical device is needed.

SUMMARY OF THE DISCLOSURE

In one embodiment of the disclosure, a medical device is disclosed. The medical device includes a housing, a power supply, a thermally conductive mounting clamp, a heat shield, and at least one fastener. The housing includes a handle. The power supply is disposed within the housing. The thermally conductive mounting clamp is attached to an outer surface of the housing. The heat shield is disposed within the housing adjacent to the power supply. The heat shield is disposed against at least one interior surface of the handle. The at least one fastener passes through at least one opening in the housing and is in thermally conductive contact with the thermally conductive mounting clamp. Heat generated by the power supply is configured to dissipate from the power supply, through the heat shield, through the at least one fastener, and into the thermally conductive mounting clamp.

In another embodiment of the disclosure, an infusion device for mounting to a pole is disclosed. The infusion device includes a housing, a thermally conductive mounting clamp, an infusion pump, a power supply, a heat shield, and at least one fastener. The housing includes a handle. The thermally conductive mounting clamp is attached to an outer surface of the housing and is configured to attach to a pole. The infusion pump is disposed within the housing. The power supply is disposed within the housing. The heat shield is disposed within the housing adjacent to the power supply. The heat shield is disposed against at least one interior surface of the handle. The at least one fastener passes through at least one opening in the housing and is in thermally conductive contact with the thermally conductive mounting clamp. Heat generated by the power supply is configured to dissipate from the power supply, through the heat shield, through the at least one fastener, and into the thermally conductive mounting clamp.

In still another embodiment of the disclosure, a method is disclosed of dissipating heat in a medical device. Heat is dissipated from a power supply within a housing, through a heat shield disposed within the housing adjacent to the power supply and against at least one interior surface of a handle of the housing, through at least one fastener passing through at least one opening in the housing and in thermally conductive contact with a thermally conductive mounting clamp, and into the thermally conductive mounting clamp.

These and other features, aspects and advantages of the disclosure will become better understood with reference to the following drawings, description and claims.

BRIEF DESCRIPTION OF THE DRAWINGS

FIG. 3 illustrates a partially disassembled view of the perspective cross-section view of FIG. 2;

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims. It is noted that the Figures are purely for illustrative purposes and are not to scale.

Figure 1:
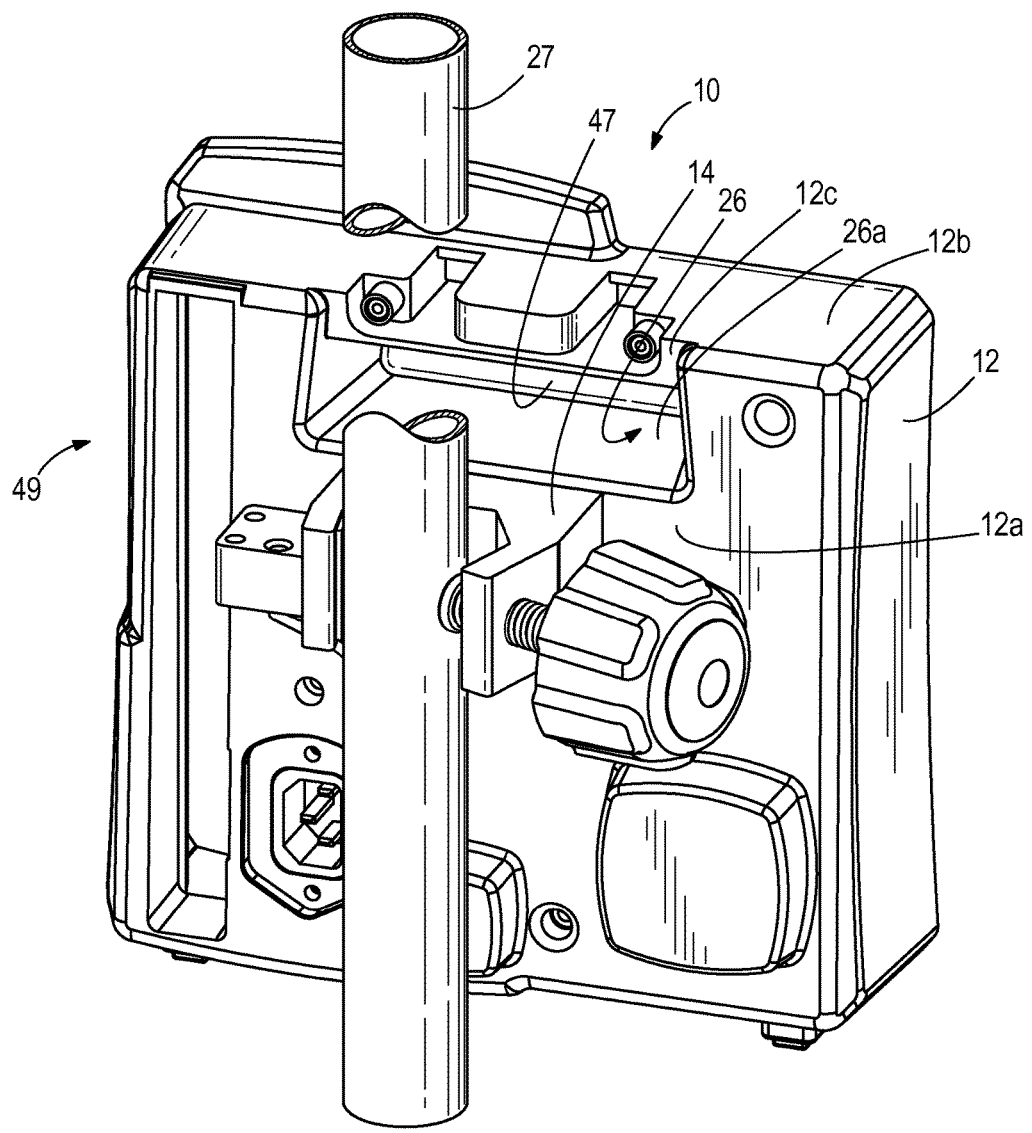
FIG. 1 illustrates a rear view of one embodiment of a medical device.
Figure 2:
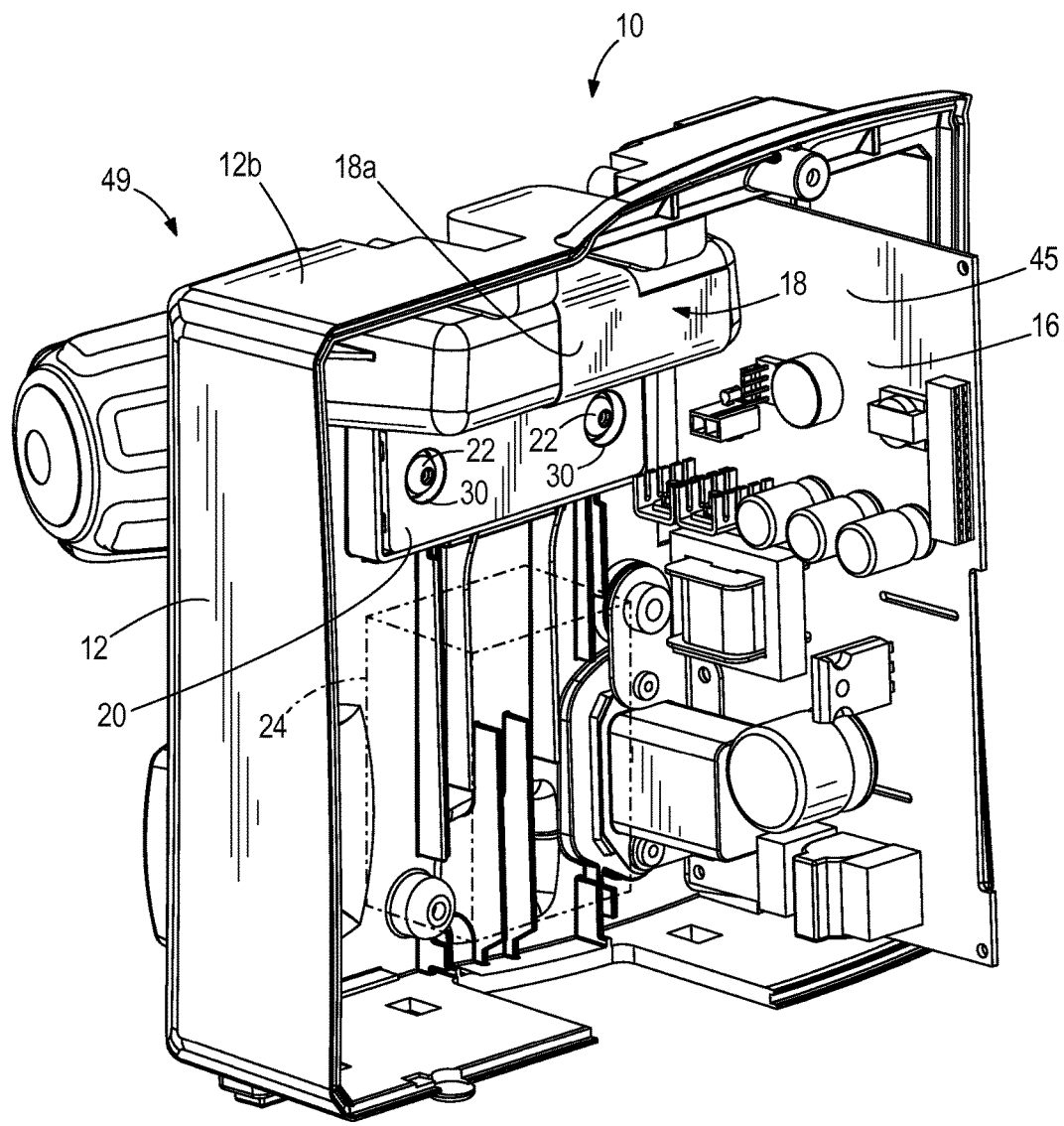
FIG. 2 illustrates a perspective cross-section view through the medical device of the embodiment of FIG. 1.

FIG. 1 illustrates a rear view of one embodiment of a medical device 10. FIG. 2 illustrates a perspective cross-section view through the medial device 10 of the embodiment of FIG. 1. FIG. 3 illustrates a partially disassembled view of the perspective cross-section view of FIG. 2. Collectively, as shown in FIGS. 1-3, the medical device 10 comprises a housing 12, a thermally conductive mounting clamp 14, a power supply 16, a heat shield 18, an electrically insulating thermally conductive bracket 20, fasteners 22, and infusion pump 24 supported by the housing 12. In other embodiments, the medical device 10 may comprise varying types of medical device unrelated to infusion pumps.

The housing 12 is made of Polycarbonate/Acrylonitrile Butadiene Styrene (PC/ABS). In other embodiments, the housing 12 may be made of varying materials. The housing 12 comprises a handle 26 external to the housing 12. The handle 26 may be gripped by a user to carry the medical device 10. In one embodiment the handle 26 is defined at least partially by a recess 26a formed in an outer surface 12a of the housing 12 adjacent to its top 12b. The recess 26a is elongated horizontally and is sized, shaped, and located to allow a typical user to insert one or more fingers into the recess 26a to move or lift the medical device 10. Since the recess 26a is adjacent to the top 12b of the housing 12, the user can also use their thumb on the top 12b of the housing 12 to improve their grip on the medical device 10. The thermally conductive mounting clamp 14 is attached to the outer surface 12a of the housing 12. The thermally conductive mounting clamp 14 allows the medical device 10 to be clamped to a structure 27 such as a pole. The thermally conductive mounting clamp 14 is made of aluminum. In other embodiments, the thermally conductive mounting clamp 14 may be made of other thermally conductive materials. The power supply 16 is disposed within the housing 12. The power supply 16 supplies power to the infusion pump 24.

The heat shield 18 is made of aluminum. The heat shield 18 is disposed within the housing 12 adjacent but apart from the power supply 16. A top portion 18a of the heat shield 18 comprises a curved, U-shape and is disposed against multiple interior surfaces 26a, 26b, 26c, and 26d of the handle 26. A bottom portion 18b of the heat shield 18 is straight. The bottom portion 18b of the heat shield 18 is disposed below the handle 26 sandwiched against and between an interior surface 12a of the housing 12 and the electrically insulating thermally conductive bracket 20. In other embodiments, the heat shield 18 may comprise varying shapes, may be made of varying thermally conductive materials, and may be disposed against any number and configuration of interior surfaces of the handle 26 or housing 12. The electrically insulating thermally conductive bracket 20 is made of a ceramic filled nylon. Preferably the thermally conductive bracket 20 comprises a plastic bracket material such as 299 X 131034 Nylon 6/6 supplied by RTP Company based out of Winona, Minn. In other embodiments, the electrically insulating thermally conductive bracket 20 may be made of varying electrically insulating but thermally conductive materials.

The fasteners 22 pass through openings 30 in the electrically insulating thermally conductive bracket 20, through openings 32 in the housing 12, into openings 34 in the thermally conductive mounting clamp 14 thereby securing the bottom portion 18b of the heat shield 18 between the electrically insulating thermally conductive bracket 20 and the interior surface 12a of the housing 12. In one embodiment at least the openings 34 in the thermally conductive mounting clamp 14 are threaded so as to matingly receive threaded fasteners 22. The fasteners 22 are in thermally conductive contact with the electrically insulating thermally conductive bracket 20 and with the mounting clamp 14. The fasteners 22 do not contact the heat shield 18. The fasteners 22 are made of steel. In other embodiments, the fasteners 22 may vary in number, may be made of varying thermally conductive materials, and may vary in configuration. Heat generated by the power supply 16 is configured to dissipate from the power supply 16 to the heat shield 18 through at least one of convection or radiation, and from the heat shield 18, through the electrically insulating thermally conductive bracket 20, through the fasteners 22, and into the thermally conductive mounting clamp 14 through conduction. In such manner, heat from the power supply 16 is dissipated using the configuration of the medical device 10 in order to cool the handle 26 to meet temperature requirements for the handle 26 of the housing 12 without requiring vents or a fan within the housing 12.

Figure 4A:
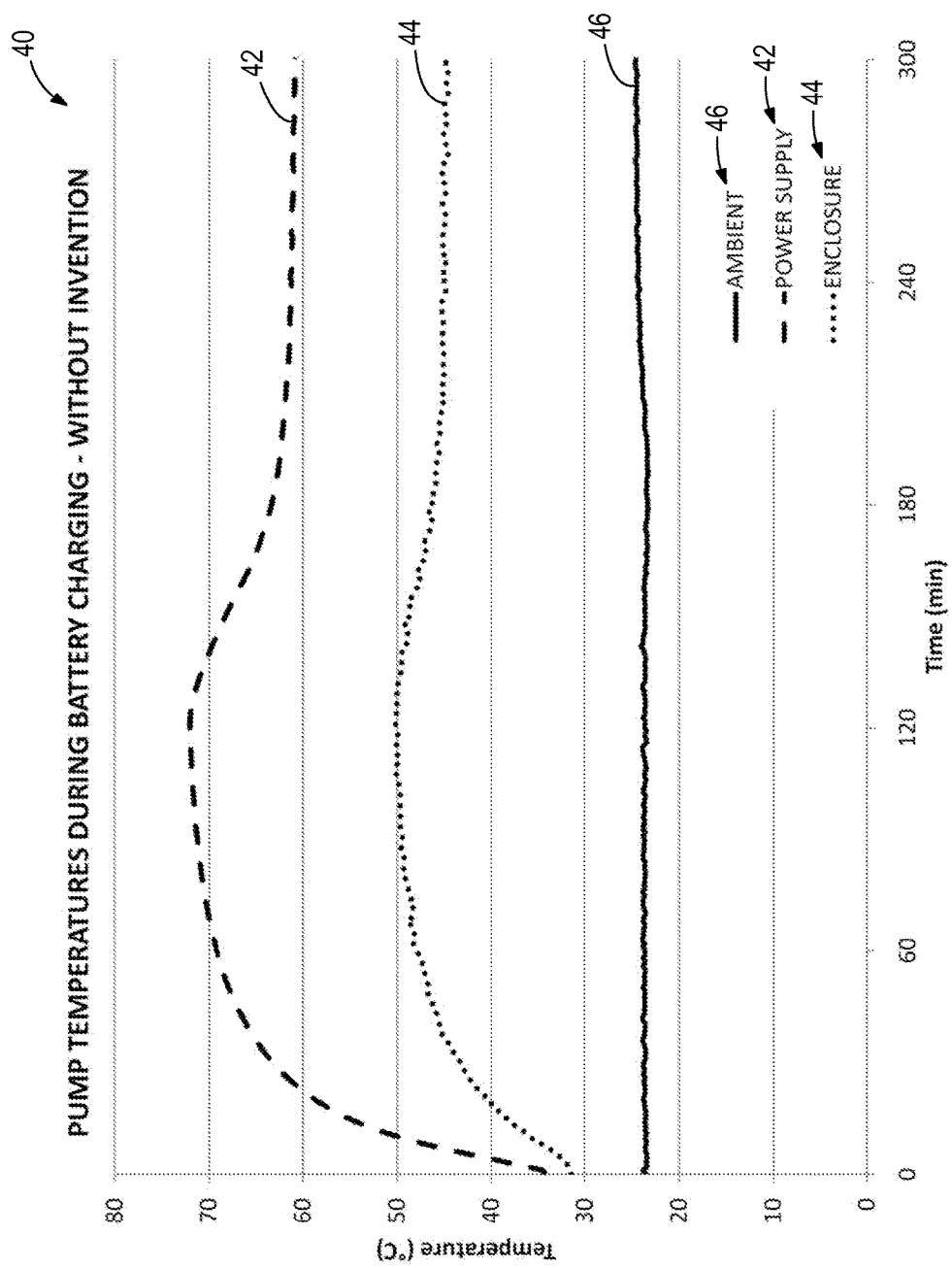
FIG. 4A illustrates a temperature versus time graph plotting temperature versus time curves which were obtained for a medical device identical to the medical device of FIGS. 1-3 but lacking the heat shield and the thermally conductive bracket of the disclosure.

FIG. 4A illustrates a temperature versus time graph 40 plotting temperature versus time curves 42, 44, and 46 which were obtained for a medical device identical to the medical device 10 of FIGS. 1-3 but lacking the heat shield 18 and the thermally conductive bracket 20 of the disclosure. Time is plotted on the X-axis in minutes and temperature is plotted on the Y-axis in degrees Celsius. Curve 42 represents the temperature versus time which was obtained, for the medical device identical to the medical device 10 of FIGS. 1-3 but lacking the heat shield 18 and the thermally conductive bracket 20 of the disclosure, at location 45 on the power supply 16 as shown in FIGS. 2 and 3 (although location 45 is shown on medical device 10 of the disclosure having the heat shield 18 and the thermally conductive bracket 20, the location tested in creating curve 42 for the medical device lacking the heat shield and the thermally conductive bracket is identical to location 45). Curve 44 represents the temperature versus time which was obtained, for the medical device identical to the medical device 10 of FIGS. 1-3 but lacking the heat shield 18 and the thermally conductive bracket 20 of the disclosure, at location 47 on the outer surface 12a of the housing 12 as shown in FIG. 1, and more specifically was obtained on a rear vertical exterior surface 12c of the recess 26a that defines the handle 26 (although location 47 is shown on medical device 10 of the disclosure having the heat shield 18 and the thermally conductive bracket 20, the location tested in creating curve 44 for the medical device lacking the heat shield and the thermally conductive bracket is identical to location 47). Curve 46 represents the temperature versus time which was obtained, for the medical device identical to the medical device 10 of FIGS. 1-3 but lacking the heat shield 18 and the thermally conductive bracket 20 of the disclosure, at location 49 which is the ambient temperature in the laboratory where the medical device 10 was tested as shown in FIGS. 1, 2, and 3 (although location 49 is shown on medical device 10 of the disclosure having the heat shield 18 and the thermally conductive bracket 20, the location tested in creating curve 46 for the medical device lacking the heat shield and the thermally conductive bracket is identical to location 49).

Figure 4B:
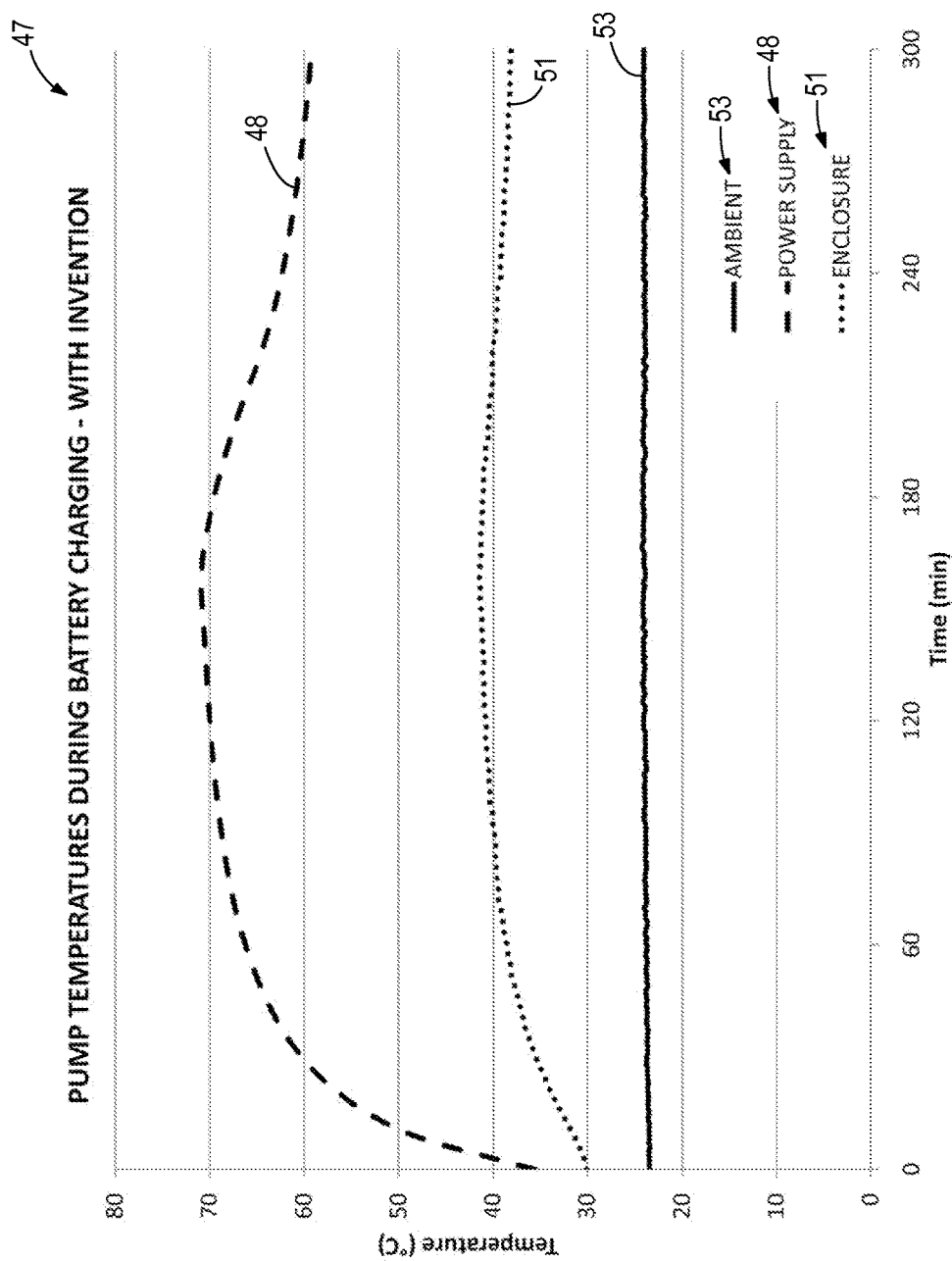
FIG. 4B illustrates a temperature versus time graph plotting temperature versus time curves which were obtained for the medical device of FIGS. 1-3 having the heat shield and the thermally conductive bracket of the disclosure.

FIG. 4B illustrates a temperature versus time graph 47 plotting temperature versus time curves 48, 51, and 53 which were obtained for the medical device 10 of FIGS. 1-3 having the heat shield 18 and the thermally conductive bracket 20 of the disclosure. Time is plotted on the X-axis in minutes and temperature is plotted on the Y-axis in degrees Celsius. Curve 48 represents the temperature versus time which was obtained, for the medical device 10 of FIGS. 1-3 having the heat shield 18 and the thermally conductive bracket 20 of the disclosure, at location 45 on the power supply 16 as shown in FIGS. 2 and 3. Curve 51 represents the temperature versus time which was obtained, for the medical device 10 of FIGS. 1-3 having the heat shield 18 and the thermally conductive bracket 20 of the disclosure, at location 47 on the outer surface 12a of the housing 12 as shown in FIG. 1, and more specifically obtained on a rear vertical exterior surface 12c of the recess 26a that defines the handle 26. A comparison of curve 44 of FIG. 4A to curve 51 of FIG. 4B demonstrates that the heat shield 18 and the thermally conductive bracket 20 of the medical device 10 of FIGS. 1-3 helped reduce the temperature obtained at location 47 on the outer surface 12a of the housing 12, and more specifically obtained on the rear vertical exterior surface 12c of the recess 26a that defines the handle 26 as shown in FIG. 1, to a level that meets the requirements of the IEC 60601-1 $3^{rd}$ Edition standard which requires the temperature of external surfaces of the housing 12 of the medical device 10 to be 60 degrees Celsius or below under certain ambient conditions. Curve 53 represents the temperature versus time which was obtained, for the medical device 10 of FIGS. 1-3 having the heat shield 18 and the thermally conductive bracket 20 of the disclosure, at location 49 which is the ambient temperature in the laboratory where the medical device 10 was tested as shown in FIGS. 1, 2, and 3.

Thus, it can be seen and appreciated by one of ordinary skill in the art that temperature versus time testing of an embodiment of a medical device lacking components of the present disclosure resulted in a temperature versus time curve at location 47 on the outer surface 12a of the housing 12 in or near the handle 26 which came close to not meeting the requirements of the IEC 60601-1 $3^{rd}$ Edition standard in an environment with an ambient temperature of approximately 25 degrees Celsius. One skilled in the art will appreciate that if the environment has an ambient temperature of 40 degrees Celsius and the medical device lacks the components of the present disclosure, the surface temperature may exceed the standard. Based on this testing, it is apparent that the use of the heat shield 18 and the thermally conductive bracket 20 allows the medical device 10 of FIGS. 1-3 to reduce its temperature to easily meet the IEC 60601-1 $3^{rd}$ Edition standard without the use of vents or a fan to lower the temperature. This reduces the power required by the medical device 10 along with reducing the likelihood that undesired fluid will enter the housing 12 of the medical device 10.

Figure 5:
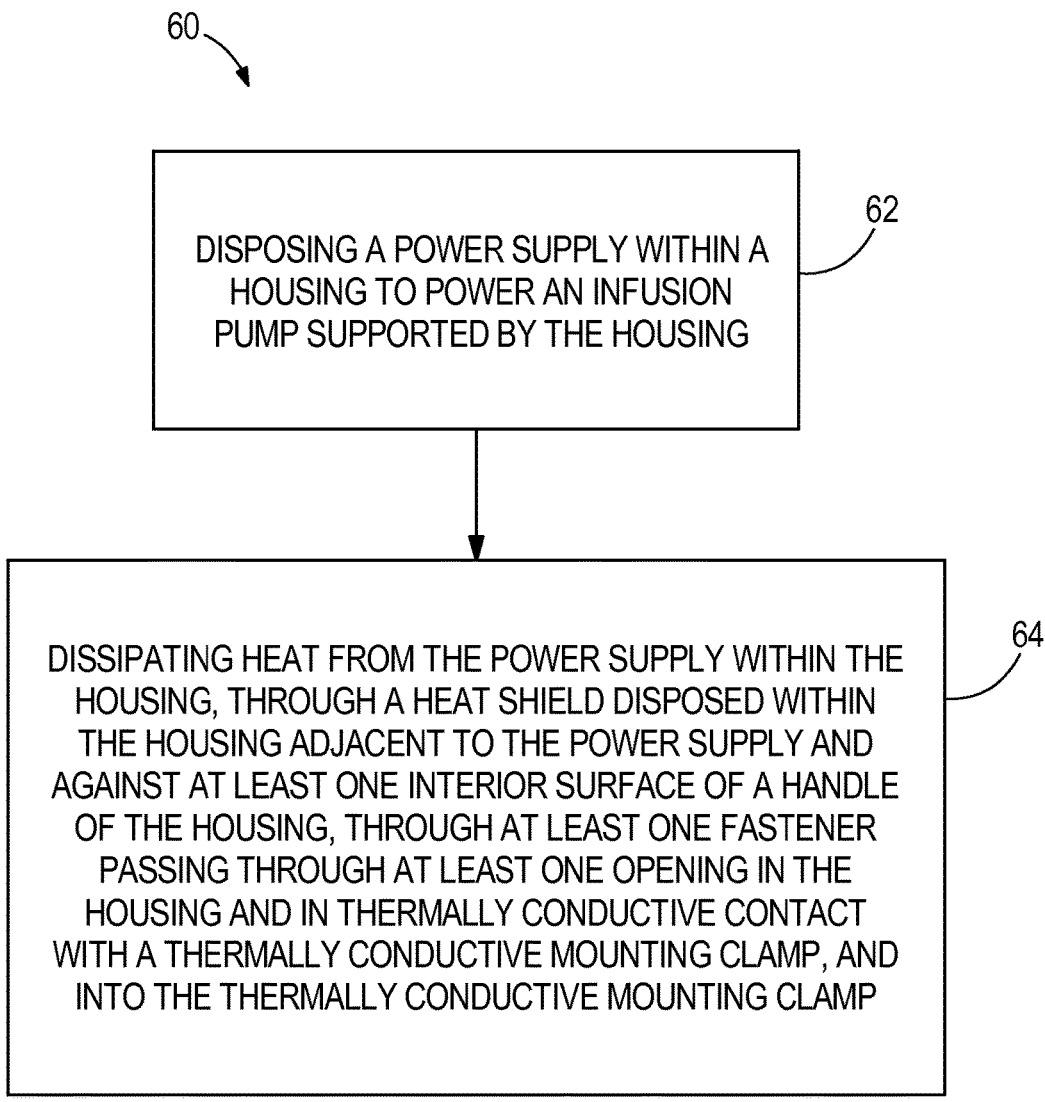
FIG. 5 illustrates a flowchart showing one embodiment of a method of dissipating heat in a medical device.

FIG. 5 illustrates a flowchart showing one embodiment of a method 60 of dissipating heat in a medical device. The method 60 may utilize any of the embodiments of the medical device disclosed herein. In step 62, a power supply disposed within a housing may power an infusion pump supported by the housing. In step 64, heat is dissipated from the power supply within the housing, through a heat shield disposed within the housing adjacent to the power supply and against at least one interior surface of a handle of the housing, through at least one fastener passing through at least one opening in the housing and in thermally conductive contact with a thermally conductive mounting clamp, and into the thermally conductive mounting clamp.

In one embodiment, step 64 may comprise the heat generated by the power supply being dissipated from the power supply to the heat shield through at least one of convection or radiation, and from the heat shield, through an electrically insulating thermally conductive bracket disposed against the heat shield within the housing, through the at least one fastener, and into the thermally conductive mounting clamp through conduction. The heat shield may be curved, may comprise a U-shape, and may be disposed against multiple interior surfaces of the handle of the housing. In other embodiments, the configuration, shape, materials, and number of components of the medical device may vary. In still other embodiments, any of the steps of the method 60 may be altered in substance or in order, may not be followed, or one or more additional steps may be added.

One or more embodiments of the disclosure may reduce one or more issues of one or more of the existing medical devices by dissipating heat generated by the medical device without requiring a fan or vents within the housing of the medical device. This may reduce the power required by the medical device along with reducing the likelihood that undesired fluid will enter the housing of the medical device.

It should be understood, of course, that the foregoing relates to exemplary embodiments of the disclosure and that modifications may be made without departing from the scope of the disclosure as set forth in the following claims.

We claim:

1. A medical device comprising:
    a housing comprising a handle, the handle defined at least partially by a horizontally elongated recess formed in an outer surface of the housing adjacent a top of the housing;
    a power supply disposed within the housing;
    a thermally conductive mounting clamp attached to the outer surface of the housing at a location remote from the handle recess;
    a heat shield disposed within the housing adjacent to the power supply, the heat shield disposed against at least one interior surface of the handle; and
    at least one fastener passing through at least one opening in the housing and in thermally conductive contact with the thermally conductive mounting clamp, wherein heat generated by the power supply is configured to dissipate from the power supply into the heat shield, the heat shield configured to conduct heat away from the handle into the at least one fastener, the heat passing from the at least one fastener into the thermally conductive mounting clamp.

2. The medical device of claim 1 further comprising an infusion pump supported by the housing.

3. The medical device of claim 1 wherein the heat shield is disposed apart from the power supply within the housing, and the heat generated by the power supply is configured to dissipate from the power supply to the heat shield through at least one of convection or radiation and from the heat shield, through the at least one fastener, and into the thermally conductive mounting clamp through conduction.

4. The medical device of claim 1 wherein the heat shield is curved.

5. The medical device of claim 1 wherein the heat shield comprises a U-shape.

6. The medical device of claim 1 wherein the heat shield is disposed against multiple interior surfaces of the handle.

7. The medical device of claim 1 further comprising an electrically insulating, thermally conductive bracket disposed against the heat shield within the housing, wherein heat generated by the power supply is configured to dissipate from the power supply, through the heat shield, through the electrically insulating, thermally conductive bracket, through the at least one fastener, and into the thermally conductive mounting clamp.

8. The medical device of claim 7 wherein the heat generated by the power supply is configured to dissipate from the power supply to the heat shield through at least one of convection or radiation and from the heat shield, through the electrically insulating, thermally conductive bracket, through the at least one fastener, and into the thermally conductive mounting clamp through conduction.

9. An infusion device for mounting to a pole comprising:
    a housing comprising a handle, the handle defined at least partially by a horizontally elongated recess formed in an outer surface of the housing adjacent a top of the housing;
    a thermally conductive mounting clamp attached to the outer surface of the housing and configured to attach to a pole;
    an infusion pump disposed within the housing;
    a power supply disposed within the housing;
    a heat shield disposed within the housing adjacent to the power supply, the heat shield disposed against at least one interior surface of the handle; and
    at least one fastener passing through at least one opening in the housing and in thermally conductive contact with the thermally conductive mounting clamp, wherein heat generated by the power supply is configured to dissipate from the power supply into the heat shield, the heat shield configured to conduct heat away from the handle into the at least one fastener, the heat passing from the at least one fastener into the thermally conductive mounting clamp.

10. The infusion device of claim 9 wherein the heat shield is disposed apart from the power supply within the housing, and the heat generated by the power supply is configured to dissipate from the power supply to the heat shield through at least one of convection or radiation and from the heat shield, through the at least one fastener, and into the thermally conductive mounting clamp through conduction.

11. The infusion device of claim 9 wherein the heat shield is curved.

12. The infusion device of claim 9 wherein the heat shield comprises a U-shape.

13. The infusion device of claim 9 further comprising an electrically insulating, thermally conductive bracket disposed against the heat shield within the housing, wherein heat generated by the power supply is configured to dissipate from the power supply, through the heat shield, through the electrically insulating, thermally conductive bracket, through the at least one fastener, and into the thermally conductive mounting clamp.

14. The infusion device of claim 13 wherein the heat generated by the power supply is configured to dissipate from the power supply to the heat shield through at least one of convection or radiation and from the heat shield, through the electrically insulating, thermally conductive bracket, through the at least one fastener, and into the thermally conductive mounting clamp through conduction.

15. A method of dissipating heat in a medical device comprising:
dissipating heat from a power supply within a housing into a heat shield disposed within the housing adjacent to the power supply, the heat shield positioned against at least one interior surface of a handle of the housing, the heat passing from the heat shield away from the handle and into at least one fastener, the at least one fastener passing through at least one opening in the housing and in thermally conductive contact with a thermally conductive mounting clamp, the heat passing into the thermally conductive mounting clamp.

16. The method of claim 15 further comprising the power supply powering an infusion pump supported by the housing.

17. The method of claim 15 further comprising the heat generated by the power supply dissipating from the power supply to the heat shield through at least one of convection or radiation and from the heat shield, through the at least one fastener, and into the thermally conductive mounting clamp through conduction.

18. The method of claim 15 wherein the heat shield is disposed against multiple interior surfaces of the handle.

19. The method of claim 15 further comprising the heat generated by the power supply dissipating from the power supply, through the heat shield, through an electrically insulating, thermally conductive bracket disposed against the heat shield within the housing, through the at least one fastener, and into the thermally conductive mounting clamp.

20. The method of claim 19 further comprising the heat generated by the power supply dissipating from the power supply to the heat shield through at least one of convection or radiation and from the heat shield, through the electrically insulating, thermally conductive bracket, through the at least one fastener, and into the thermally conductive mounting clamp through conduction.

* * * * *